United States Patent [19]
Lichtenwalter et al.

[11] Patent Number: 5,352,582
[45] Date of Patent: Oct. 4, 1994

[54] HOLOGRAPHIC BASED BIO-ASSAY

[75] Inventors: Kay Lichtenwalter, San Jose; Hewlett E. Melton, Jr., Sunnyvale, both of Calif.

[73] Assignee: Hewlett-Packard Company, Palo Alto, Calif.

[21] Appl. No.: 144,919

[22] Filed: Oct. 28, 1993

[51] Int. Cl.$^5$ .................. C12Q 1/68; G01N 33/543
[52] U.S. Cl. ........................... 435/6; 359/1; 359/3; 422/82.05; 430/1; 430/2; 435/4; 435/7.1; 435/808; 436/501; 436/518; 436/535; 436/805
[58] Field of Search ............ 436/501, 518, 535, 805, 436/807; 435/4, 6, 7.1, 808; 422/82.05; 359/1, 3, 10, 30, 32, 33; 430/1, 2

[56] References Cited

U.S. PATENT DOCUMENTS 5,166,813  11/1992  Metz ..................... 359/1

OTHER PUBLICATIONS

Pluddemann, E. P. "Silane Coupling Agents", Plenum, N.Y. 1982.

Partis; M. D., D. G. Griffiths, G. C. Roberts and R. B. Beechey, 1983, Cross-linking of protein by w-maleimido alkanoyl n-hydroxysuccinimido esters. J. Prot. Chemistry, 2, 263.

Kremsky, J. N., J. L. Wooters, J. P. Dougherty, R. E. Meyers, M. Collins and E. L. Brown. 1987. Immobilization of DNA via oligonucleotides containing an aldehyde or carboxylic acid group at the 5' terminus. Nuc. Acids Research, 15, 2891.

Lund, V., R. Schmid, D. Rickwood, and E. Hornes. 1988. Assessment of methods for covalent binding of nucleic acids to magnetic beads, Dynabeads and the characteristics of the bound nucleic acids in hybridization reactions. Nuc. Acids Research, 16, 10861.

Bhatia, S. K., L. C. Shriver-Lake, K. J. Prior, J. H. Georger, J. M. Calvert, R. Bredehorst and F. S. Ligler. 1989. Use of thiol-terminal silanes and heterobifunctional crosslinkers for immobilization of antibodies on silica surfaces. Anal. Biochem., 178, 408.

Running, J. A. and M. S. Urdea. 1990. A procedure for productive coupling of synthetic oligonucleotides to polystyrene microtiter wells for hybridization capture. Bio Techniques, 8, 276.

*Primary Examiner*—David Saunders

[57] ABSTRACT

An apparatus detects a target reactant that binds to an immobilized reactant. The apparatus generates a holographic image at a predetermined location when the reactants are present and bound to one another. The immobilized reactant is bound to a support surface at selected locations. The locations are chosen such that a holographic plate is generated when the target reactant binds to the immobilized reactant. An associated method may be used to detect antibody-antigen reactions, the binding of two strands of nucleic acid, the binding of an enzyme to one of its substrates, and so on.

19 Claims, 3 Drawing Sheets

HOLOGRAPHIC BASED BIO-ASSAY

FIELD OF THE INVENTION

The present invention relates to biological assays, and more particularly, to an improved method and apparatus for detecting the binding of an organic molecule of interest to a substrate.

BACKGROUND OF THE INVENTION

Reactions between biological molecules exhibit an extremely high degree of specificity. It is this specificity that provides a living cell with the ability to carry out thousands of chemical reactions simultaneously in the same "vessel". In general, this specificity arises from the "fit" between two molecules having very complex surface topologies. For example, an antibody binds a molecule displaying an antigen on its surface because the antibody contains a pocket whose shape is the complement of a protruding area on the antigen. This type of specific binding between two molecules forms the basis of numerous biological assays.

For example, the binding between an antibody and molecules displaying a particular antigenic group on their surface may be used as the basis for detecting the presence of the antibody, molecules carrying the antigenic group, or the antigenic group itself. This type of assay forms the basis of numerous medical diagnostic tests. All of these tests depend on detecting and measuring the binding of an antibody molecule that is specific for a particular antigenic group to a molecule carrying the group in question. In general, one of the two molecular species is immobilized on a support surface where it acts as a "glue" for binding the other species. In one class of assays, in which either the antibody or the molecule carrying the antigenic group is to be assayed, one of the two species is covalently immobilized to the support and the other is free in solution. The immobilized species is exposed to the solution that may contain the soluble species and the amount of material bound to the immobilized species after the exposure is measured. In a second class of assays in which the antigenic group itself is to be assayed, one of the two species is covalently immobilized to the support and the other is electrostatically bound to the covalently immobilized species. A solution containing a small molecule having the antigenic group thereon will interfere with the electrostatic binding. This leads to the release of the electrostatically bound species. These assays detect the degree of release of the electrostatically bound species.

Antibodies and antigen carrying molecules are but one of a number of classes of biological molecules whose binding can form the basis of an analytic procedure. For example, nucleic acids are linear polymers in which the linked monomers are chosen from a class of 4 possible sub-units. In addition to being capable of being linked together to form the polymers in question, each unit has a complementary sub-unit to which it can bind electrostatically. For example, in the case of DNA, the polymers are constructed from four bases that are usually denoted by A, T ,G, and C. The bases A and T are complementary to one another, and the bases G and C are complementary to one another. Consider two polymers that are aligned with one another. If the sequences in the polymers are such that an A in one chain is always matched to a T in the other chain and a C in one chain is always matched to a G in the other chain, then the two chains will be bound together by the electrostatic forces. Hence, an immobilized chain can be used to bind the complementary chain. This observation forms the basis of tests that detect the presence of DNA or RNA that is complementary to a known DNA or RNA chain. Such detection forms the basis of a number of medical and/or diagnostic tests.

While this type of specific electrostatic binding provides a high degree of specificity, the amount of material that is bound is usually quite small. This makes the detection of the binding between the reactants difficult. Numerous inventions have been directed to overcoming this problem.

The most sensitive techniques are based on the use of radioisotopes. Unfortunately, any reaction requiring the use of such isotopes presents safety issues which essentially eliminate the assay from being used outside the research laboratory. There are a number of tests that use various labeled chemicals to detect the amount of target material bound to a substrate. Additionally, a sequence of reactants can be bound to the target reactant for purposes of increasing the sensitivity. These tests require the operator to perform a number of processing steps after the reactants have been given a chance to bind. These additional steps detract from the tests in question. In addition, expensive additional radioactive and/or otherwise labeled chemicals are required.

Techniques that measure the binding of the reactants without the need to add radioactive or otherwise labeled chemicals are also known to the art. In one such technique, the reactant that is immobilized on the surface is patterned to form an optical grating. This is accomplished by immobilizing a layer of the reactant to the surface and then inactivating regular strips of the immobilized reactant. The remaining periodic strips will bind the complementary reactant. When the surface is illuminated with a coherent light source such as a laser, the remaining periodic strips act as an optical grating. The presence of the bound material increases the thickness of the strips and may be detected by shifts in the diffraction pattern generated by the grating. While this technique does not require the complex chemistry of the prior art techniques described above, it has two problems that limit its usefulness. First, the system requires optical components such as lenses to direct the selected diffraction order onto an optical detector. Second, the signal energy is distributed among the various diffraction orders in a one-dimensional fashion; hence, the amount of light available for detection is small.

SUMMARY OF THE INVENTION

The present invention comprises an apparatus and method for detecting a target reactant that binds to a capture reactant. The apparatus includes a support structure on which the capture reactant is immobilized at selected locations. The capture reactant binds the target reactant when the target and capture reactants are brought into contact with one another. The locations at which the capture reactant is immobilized are chosen such that a holographic image is generated at a predetermined image location when the capture reactant is bound to the target reactant, and the bound reactants are illuminated with coherent light.

DETAILED DESCRIPTION OF THE INVENTION

Figure 1:
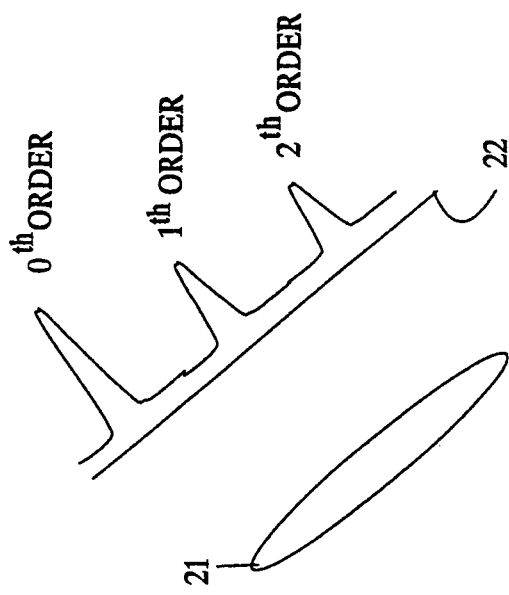
FIG. 1 illustrates the measurement of antibody-antigen binding using a step grating.
Figure 1:
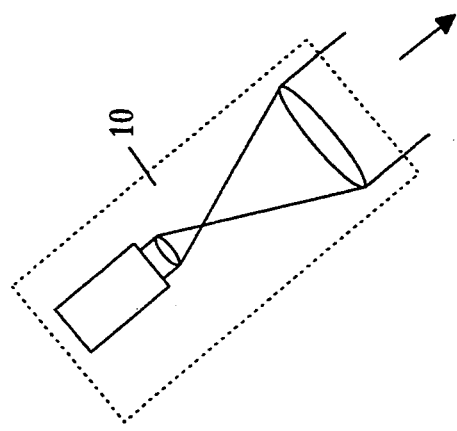
Figure 1:
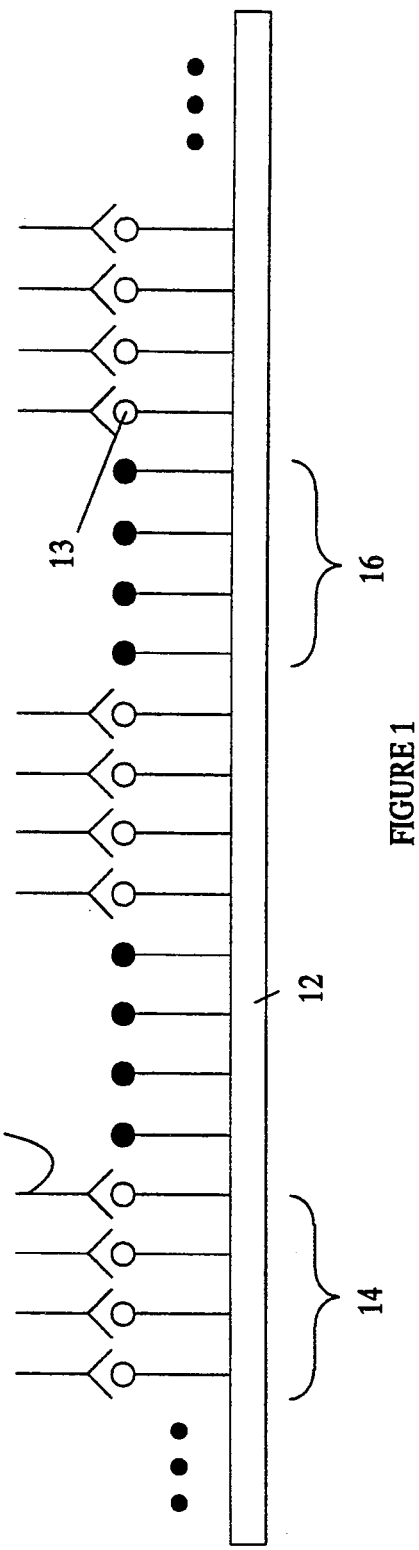

The present invention utilizes a hologram to overcome the problems encountered in systems that utilize diffraction grating effects to measure the binding of the reactants. The present invention may be more easily understood with reference to such a grating system. FIG. 1 illustrates the measurement of binding of a soluble target reactant 18 to a reactant 13 that has been covalently immobilized onto substrate 12. Periodic linear bands are created in the immobilized capture reactant layer by exposing strips of the immobilized reactant to ultra violet light of sufficient intensity to deactivate the binding sites on the immobilized reactant. An exemplary exposed periodic linear strip is shown at 16. The exposure is carried out by using a shadow mask to limit the exposure to the desired periodic linear strips. The remaining strips 14 are capable of binding the soluble target reactant. The presence of target reactant 18 in a solution is detected by bringing the solution in contact with the immobilized reactant 13. The unbound reactant is then washed away. The surface is then illuminated with a coherent light source 10. The light reflected from the surface is imaged onto a screen 22 by at least one lens 21. The presence of target material bound on periodic linear strips 14 increases the height of these strips. The resultant structure is equivalent to an optical step grating. The grating gives rise to a one-dimensional interference pattern that is formed on the screen. If the light source is monochromatic, the one-dimensional pattern will consist of bright bands at those locations at which the optical path length from the surface, through the optics and to the screen is an integer multiple of the wavelength. A detector may be placed at the locations of the maxima to detect the presence of the interference pattern.

While the system shown in FIG. 1 represents an improvement over systems requiring some form of chemicals, radioactive or otherwise labeled, it requires optical components such as lens 21. These components increase the cost and complexity of the system. In addition, the reflected light intensity is divided between the various diffraction orders. This reduces the signal to noise ratio that can be obtained. Finally, the presence of any liquid meniscus between support 12 and lens 21 can lead to optical distortions that alter the location and/or intensity of the diffraction maxima.

Figure 2:
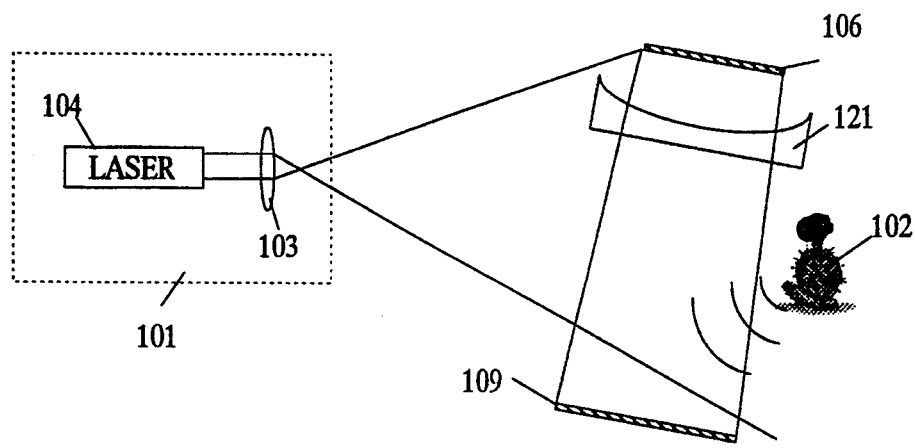
FIG. 2 illustrates the manner in which a holographic plate is generated.

The present invention avoids these problems by using a system based on holography. Instead of creating a pattern of stripes on the support surface, the present invention utilizes a hologram pattern. Referring to FIG. 2, a hologram provides a means for reproducing a three-dimensional image of an object 102 utilizing light-wave patterns recorded on a photographic plate 109. The object is illuminated with a coherent beam of light produced by coherent light source 101 comprising laser 104 and lens 103. The beam is split into two parts, a reference beam and an illuminating beam. The reference beam is generated by mirror 106 and is directed onto photographic plate 109 through a distorting interface 121. The reason for the inclusion of distorting interface 121 will be discussed in more detail below. The other beam is reflected from the object onto the photographic plate. The reference beam's intensity is made to be larger than that from the object so that the amplitude and phase of the electric field caused by reflection of light by the object is faithfully recorded on the photographic plate 109.

Figure 3:
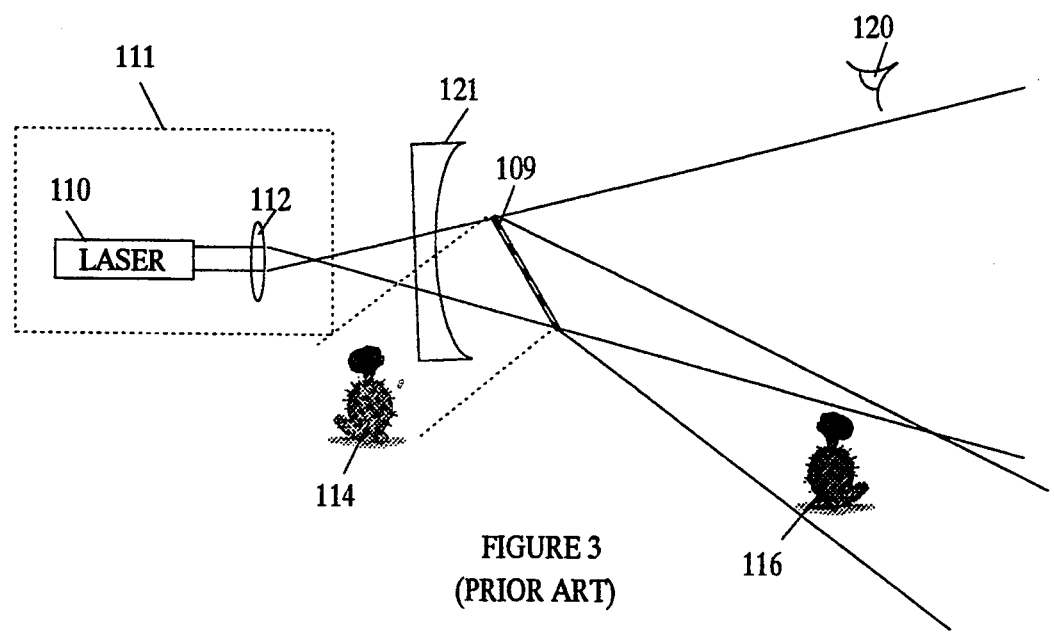
FIGS. 3 illustrates the manner in which a hologram is generated from a holographic plate.

Referring to FIG. 3, when photographic plate 109 is developed and illuminated with the aid of coherent light source 111 comprising laser 110 and lens 112 having coherent light of the same frequency and spatial illumination as that used to form the plate, including the distorting interface 121, two three-dimensional images become visible to an observer 120. One of the transmitted wave components is an exact duplication of the original waves leaving the object. This wave component appears to originate from the object, and accordingly generates a virtual image 114 of the object. The virtual image appears to an observer to exist in three-dimensional space behind photographic plate 109. Since this image is a virtual image, a lens is required to view it. In the case shown in FIG. 3, the lens is provided by the viewer's eye.

A second image 116 is generated by the conjugate phase wave component which focuses of its own accord to form a real image in space between the observer and the transparency. An object that is reproduced in three dimensions by optical systems so that the observer experiences the original object, is generally of less utility than the virtual image because its parallax relations are opposite to those of the original object. However, for the purposes of the present invention, image 116 is the more useful image since it forms without the need to introduce lenses.

The present invention utilizes an entrained hologram to measure the binding between an immobilized reactant and a soluble reactant. The bound reactant is arranged in a pattern corresponding to the fringe lines of a holographic plate of a small reflective object. The manner in which this is accomplished will be discussed in more detail below. When the soluble reactant becomes bound to the immobilized reactant, the intensity of the fringe lines increases. The holographic plate is then exposed to a suitable coherent light source, the extent of the binding is determined by measuring the intensity of the real image generated by the hologram. Furthermore, a sequence of reactants can be bound to the target reactant for purposes of increasing the sensitivity of the holographic method.

Figure 4:
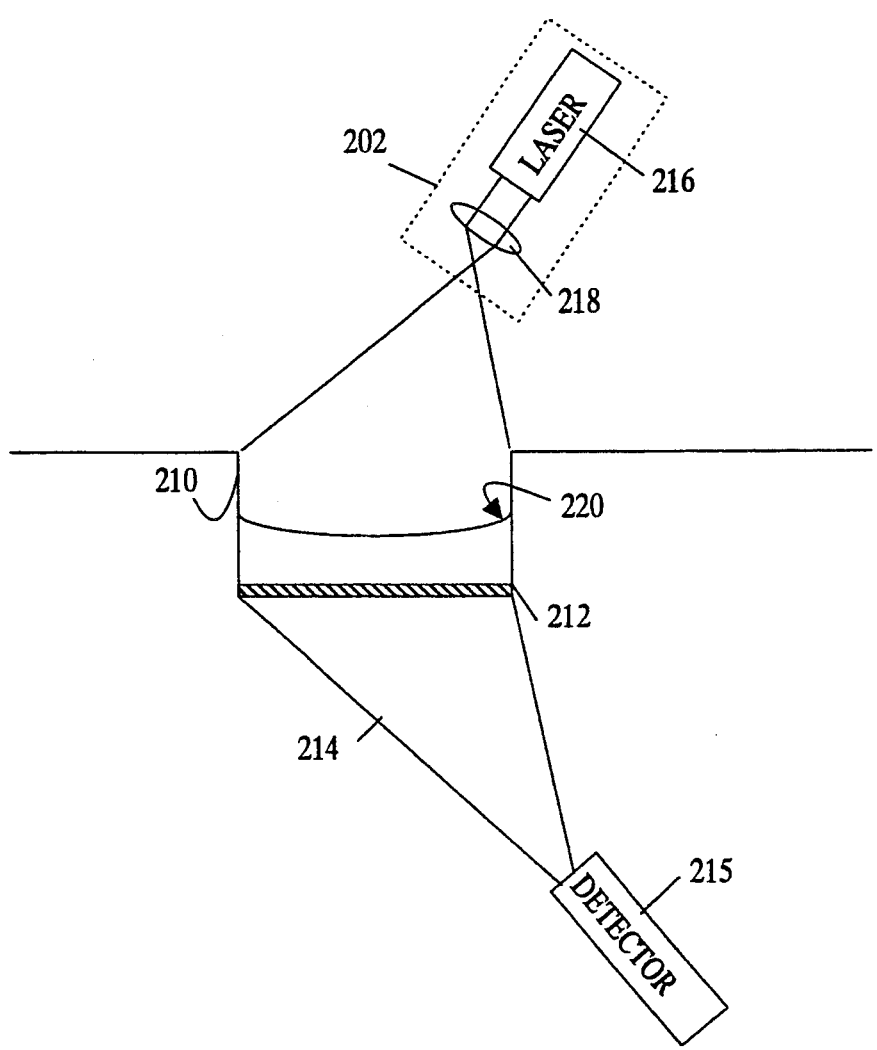
FIG. 4 is a cross-sectional view of an assay apparatus according to the present invention.

FIG. 4 is a cross-sectional view of one embodiment of the invention. A sample well 210 includes a holographic plate 212 having an entrained hologram based on an immobilized reactant. The hologram will generate a small bright object when illuminated if a sufficient concentration of a soluble reactant that binds to the immobilized reactant is present in sample well 210. Sample well 210 is illuminated with coherent light by the light source 202 comprising laser 216 and lens 218. An optical detector 215 is placed at the location of the real image generated by holographic plate 212 through the distorting interface of the meniscus 220.

It should be noted that the generation of the holographic image will still take place even if the sample well includes liquid having a meniscus 220 which alters the pattern of illumination of holographic plate 212 provided a similar distorting interface is introduced into the reference beam when the hologram is generated. Hence, the present invention provides a significant advantage over systems based on diffraction gratings, since such systems do not function properly in the presence of such distortions. In addition, no optical components are required to form the real image, hence, the present invention requires a less expensive and less complicated optical system than a system based on the generation of a diffraction grating by the binding reaction.

The manner in which holographic plate 212 is constructed will now be discussed in more detail. There are two classes of holographic plates that will be referred two as two-dimensional and three-dimensional plates, respectively. A two-dimensional plate is one in which the entrained hologram is confined to a surface. The thickness of such a hologram is small compared to the wavelength of the light used to make the hologram. In contrast, a three-dimensional plate has a hologram that is entrained in a volume whose thickness is greater than, or on the order of, the wavelength of the light in question.

Two-dimensional plates may be constructed by using a shadow mask and a suitable light source to either activate or inactivate areas on a layer of the immobilized reactant. A two-dimensional hologram may be thought of as a pattern of complex fringes on the plate. The pattern can be generated by making a hologram on a suitable photographic media in the manner described with reference to FIG. 1 above including distorting interfaces. In the case of a simple image such as a bright point source, the pattern that would be formed on the photographic plate may be calculated and used to make a mask directly by electron beam lithography.

The simplest method for generating the entrained hologram is to inactivate areas on a layer of the immobilized reactant. Reactions for attached nucleic acids and proteins to the surface of a plastic support such as a polycarbonate sheet or well are well known to those skilled in the art, and hence, will not be discussed in more detail here. The reader is directed to the list of references cited below for the details of such attachment protocols. For the purpose of the present discussion, it is sufficient to note that proteins may be attached to such substrates by the amino group of the amino acids. Similar reactions are available for nucleic acids. Once a layer of the immobilized reactant has been deposited, the areas that are not to bind the soluble reactant are inactivated. The simplest method for inactivating these areas is to expose the areas to UV light or x-rays. Exposure to radiation in the 254–260 nm range at a power density of 8 to 20 mW/cm$^2$ for a period of 1 to 120 minutes is sufficient to inactivate most proteins and nucleic acids. The exact exposure parameters must be determined for each immobilized reactant. A mercury-xenon lamp may be used for the light source. The areas that are not to be exposed are protected by the shadow mask which is a negative of the holographic pattern generated by the apparatus shown in FIG. 1.

The inactivation of nucleic acids can be enhanced by using photochemical agents such as furcoumarins or phenanthridinium halides. These agents intercalate and link the nucleic acid molecules so as to prevent the molecules from binding or hybridizing with complementary nucleic acid strands. Exemplary agents are psoralens, angelicins, ethidium bromide, and the acridine dyes. The non-active regions are created by exposing the areas to be inactivated to radiation in 300–390 nm range for 30 to 120 minutes in Tris-EDTA buffer at pH 7.5 in the presence of the enhancing agent. The concentration of the enhancing agent depends on the concentration of the immobilized reactant. For most purposes, a ratio of 1:10 nucleic acid to enhancing agent is sufficient to inactivate the nucleic acid.

In addition to photo-inactivation, the layer may be inactivated by electron beam lithography in which an electron beam is directed against the areas to be inactivated. The inactivation pattern may be determined mathematically for simple holographic images. For more complex holograms, data specifying the regions to be inactivated may be obtained by scanning a holographic plate made by the apparatus shown in FIG. 1.

An alternative method for generating a holographic pattern is to inactivate the entire layer of immobilized reactant and then photo-reactivate the appropriate regions. The inactivation involves attaching protective groups to the immobilized reactant that prevent the binding between the immobilized and soluble reactants. These groups are then removed in selected areas with the aid of an appropriate light source and shadow mask. Examples of protective groups are nitroveratryloxycarbonyl, nitrobenzyloxycarbonyl, dimethyl-dimethoxybenzloxy carbonyl, and 2-oxymethylene orthraquinone. A typical reactivation reaction would involve treating with nitroveratryloxycarbonyl and then exposing the regions to be reactivated with light at a wavelength of 362 nm and power density of 14 mW/cm$^2$ for 10 minutes in a solution of dioxane.

Three-dimensional holographic plates have the advantage of increased signal to noise. There is a limit to the amount of immobilized reactant that can be deposited on a surface; as a result, the brightness of the hologram generated by this surface is limited. If, however, the hologram is entrained in a three-dimensional structure, this limitation is substantially reduced. In addition, the three-dimensional holographic plate provides increased brightness because of interference between the light refracted by the fringes at different depths within the 3-D hologram.

A three-dimensional holographic plate may not be generated by a shadow mask. The material in which the immobilized reactant is constrained must be sufficiently porous to allow the target reactant to penetrate the material and any unbound soluble reactant to be washed out. Aerogels provide such a support. The preferred embodiment of the present invention utilizes an activation reaction to generate the fringes, since these reactions do not require the negative of the hologram plate. The 3-D holographic plate may then be placed in an apparatus such as that described with reference to FIG. 1 for exposure.

What is claimed is:

1. An apparatus for detecting a target reactant, said apparatus comprising:
    a support structure;
    a coherent light source;
    a second reactant immobilized on said support structure at selected locations thereon, said locations corresponding to a predetermined pattern, said immobilized reactant binding said target reactant when said target and immobilized reactants are brought into contact with one another, wherein said predetermined pattern causes a holographic image to be generated at a predetermined image location when said immobilized reactant is bound to said target reactant and said bound reactants are illuminated by said coherent light source; and
    detection means for detecting said holographic image.

2. The apparatus of claim 1 wherein one of said target and immobilized reactants is an antibody or antigen.

3. The apparatus of claim 1 wherein one of said target and immobilized reactants is a nucleic acid.

4. The apparatus of claim 1 wherein one of said target and immobilized reactants is an enzyme.

5. The apparatus of claim 1 wherein one of said target and immobilized reactants is a protein.

6. The apparatus of claim 1 wherein one of said target and immobilized reactants is a polypeptide.

7. The apparatus of claim 1 wherein said support structure comprises a well having said immobilized reactant bound to the bottom surface of said well.

8. The apparatus of claim 1 wherein said support structure comprises a layer of porous material having a thickness greater than the wavelength of said coherent light, and wherein said immobilized reactant is dispersed throughout said layer.

9. The apparatus of claim 1 wherein said predetermined pattern compensates for any distorting interfaces between said support structure and said coherent light source.

10. The apparatus of claim 1 wherein said holographic image comprises an image of a small bright object.

11. A method for detecting a target reactant, said method comprising the steps of:
bringing said target reactant into contact with an immobilized reactant that is immobilized on a support structure at selected locations thereon, said locations corresponding to a predetermined pattern, said immobilized reactant binding said target reactant when said target and immobilized reactants are brought into contact with one another, wherein said predetermined pattern causes a holographic image to be generated at a predetermined image location when said immobilized reactant is bound to said target reactant and said bound reactants are exposed to coherent light;
illuminating said support structure with a coherent light source; and
measuring the intensity of light at said image location.

12. The method of claim 11 wherein one of said target and immobilized reactants is an antibody or antigen.

13. The method of claim 11 wherein one of said target and immobilized reactants is a nucleic acid.

14. The method of claim 11 wherein one of said target and immobilized reactants is an enzyme.

15. The method of claim 11 wherein one of said target and immobilized reactants is a protein.

16. The methods of claim 11 wherein one of said target and immobilized reactants is a polypeptide.

17. The method of claim 11 wherein said support structure comprises a well having said immobilized reactant bound to the bottom surface of said well.

18. The method of claim 11 wherein said support structure comprises a layer of porous material having a thickness greater than the wavelength of said coherent light, and wherein said immobilized reactant is dispersed throughout said layer.

19. The method of claim 11 wherein said predetermined pattern compensates for any distorting interfaces between said support structure and said coherent light source.

* * * * *